(12) United States Patent
Tarlano

(10) Patent No.: US 6,879,658 B2
(45) Date of Patent: Apr. 12, 2005

(54) VIRUS RETARDATION METHOD AND APPARATUS

(76) Inventor: John P. Tarlano, 6912 Sydenstricker Rd., Springfield, VA (US) 22152

( * ) Notice: Subject to any disclaimer, the term of this patent is extended or adjusted under 35 U.S.C. 154(b) by 162 days.

(21) Appl. No.: 10/445,614

(22) Filed: May 27, 2003

(65) Prior Publication Data
US 2004/0240610 A1 Dec. 2, 2004

(51) Int. Cl.⁷ .................................................. A61N 5/10
(52) U.S. Cl. ......................................................... 378/65
(58) Field of Search ...................... 378/64, 65; 604/20, 604/21; 607/96, 100

(56) References Cited

U.S. PATENT DOCUMENTS 5,044,006 A * 8/1991 Cyrulnik ..................... 378/145

* cited by examiner

Primary Examiner—Craig E. Church
Assistant Examiner—Thomas R Artman

(57) ABSTRACT

An X-ray apparatus for retarding a virus in a human body is disclosed. The X-ray apparatus has four X-ray guns. Each of the four X-ray guns generating a separate frequency of an X-ray burst. A virus retardation method is also disclosed. The human body is irradiated with a series of bursts of X-rays, the X-ray bursts having a series of frequencies tuned to energize four different amino acid bases of RNA of the virus.

2 Claims, 1 Drawing Sheet

VIRUS RETARDATION METHOD AND APPARATUS

In the past, a spread of a virus that entered a human body, was attempted to be retarded by means of a chemical. However the virus could not be directly retarded in the human body after the virus entered the human body.

The present method and apparatus directly effects a virus that has entered a human body by means of X-ray bursts. The present method relates to irradiating a human body with a series of X-ray bursts, to energize a section of RNA of the virus within a human body. The X-ray bursts that effect amino acid bases on the backbone of the virus, are used. The X-rays bursts, that have selected frequencies and selected energy levels, to effect the bases in the RNA of a virus, are used to irradiate a human body. RNA of a virus within a human body that has been infected by the virus, is retarded in its spread and existence.

The method further relates to a step of determining a sequence of bases that are in a a section of an RNA helix strand of RNA of the virus. A sequence of frequencies, for a series of bursts of X-rays needed to effect a section of a complete strand of RNA of the virus, is determined. The series of bursts of X-ray irradiation of the body is generated, to cover the series of bases of at least the determined section of RNA.

In a preferred embodiment, a series of amino acid bases of a section of a SARS virus, is determined. A series of approximately 20 bases is determined.

An X-ray burst having a frequency of 9.25 (10exp16) cycles per second, corresponding to 383 electron volts, is used to energize a T amino acid base in the series of bases. An X-ray burst having a frequency corresponding to 268 electron volts, is used to energize a G base in the series of bases. An X-ray burst having a frequency corresponding to 283 electron volts, is used to energize an A amino acid base in the series of bases. An X-ray burst having a frequency of corresponding to 392 electron volts, is used to energize a C amino acid base in the series of bases.

The series of bursts of X-rays is made to irradiate a human body, that has been infected with a virus, for a time duration such as 200 seconds. Twenty bases are covered with a 10 second time interval between two successive X-ray bursts.

The above 383 and 392 electron volt frequencies of x-ray bursts are absorbed by nitrogen atoms of the T and C amino acid bases of the virus. The above 283 and 268 electron volt frequencies of x-ray bursts are absorbed by carbon atoms of the A and G amino acid bases of the virus.

Nitrogen-hydrogen type hydrogen bonds, made by T and C amino acid bases of the RNA of the virus, are effected by the described X-ray bursts. Carbon-hydrogen type hydrogen bonds, made with A and G amino acid bases of the RNA of the virus, are effected by the described X-ray bursts. Hydrogen bonds with the amino acid bases of the virus are effected by the X-ray bursts.

The X-ray bursts are generated by four X-ray guns of an X-ray apparatus. The X-ray dose level from the X-ray guns is kept low compared with a normal chest x-ray level.

SUMMARY OF THE INVENTION

An X-ray apparatus for retarding a virus in a human body comprising four X-ray guns, each of the four X-ray guns generating a separate frequency of an X-ray burst, a first separate frequency tuned to energize an amino acid base A, a second separate frequency tuned to energize an amino acid base G, a third separate frequency tuned to energize an amino acid base T, and a fourth separate frequency tuned to energize an amino acid base C.

DESCRIPTION OF THE PREFERRED EMBODIMENT

Figure 1:
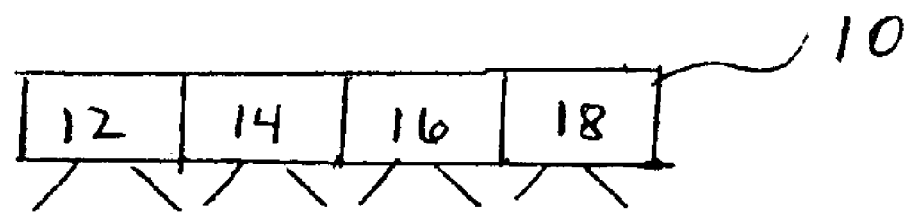
FIG. 1 is a perspective view of apparatus having four X-ray guns, the apparatus for irradiating a human body with a series of X-ray bursts from the X-ray guns.
Figure 1:

FIG. 1 shows an X-ray apparatus 10. The x-ray apparatus 10 has an X-ray gun 12, an X-ray gun 14, an X-ray gun 16, and an X-ray gun 18. Each X-ray gun generates a burst of X-rays having a separate selected frequency. X-ray gun 12 generates a burst of X-rays having a frequency of 383 electron volts. X-ray gun 14 generates a burst of X-rays having a frequency of 392 electron volts. X-ray gun 16 generates a burst of X-rays having a frequency of 283 electron volts. X-ray gun 18 generates a burst of X-rays having a frequency of 267 electron volts.

The X-ray machine 10 irradiates a human body 20 with a series of bursts of X-rays, each burst having a frequency selected to hit an amino acid base of section of RNA of a SARS virus in a human body 10.

Each base of a series of amino acid bases AAATGGGAC-CTTATTATTAG of a

What is claimed is:

1. An X-ray apparatus for retarding a virus in a human body, comprising four X-ray guns, each of the four X-ray guns generating a separate frequency of an X-ray burst, a first separate frequency tuned to energize an amino acid base A, a second separate frequency tuned to energize an amino acid base G, a third separate frequency tuned to energize an amino acid base T, and a fourth separate frequency tuned to energize an amino acid base C.

2. A virus retardation method, comprising irradiating a human body with a series of bursts of X-rays, the X-ray bursts having a series of frequencies, a first separate frequency tuned to A amino acid base, a second separate frequency tuned to G amino acid base, a third separate frequency tuned to T amino acid base, and a fourth separate frequency tuned to C amino acid base.

* * * * *